United States Patent [19]

Weisshaupt

[11] Patent Number: 5,584,844
[45] Date of Patent: Dec. 17, 1996

[54] INSTRUMENT FOR SURGICAL PURPOSES

[75] Inventor: Dieter Weisshaupt, Immendingen, Germany

[73] Assignee: AESCULAP AG, Tuttlingen, Germany

[21] Appl. No.: 535,300

[22] PCT Filed: Apr. 13, 1994

[86] PCT No.: PCT/EP94/01149

§ 371 Date: Nov. 17, 1995

§ 102(e) Date: Nov. 17, 1995

[87] PCT Pub. No.: WO94/26180

PCT Pub. Date: Nov. 24, 1994

[30] Foreign Application Priority Data

May 19, 1993 [DE] Germany .......................... 43 16 768.3

[51] Int. Cl.⁶ .................................................. A61B 17/32
[52] U.S. Cl. ........................................... 606/170; 606/208
[58] Field of Search .................................... 606/208, 170, 606/205, 206, 207, 208, 174; 128/755, 751, 753, 754

[56] References Cited

U.S. PATENT DOCUMENTS

| | | |
|---|---|---|
| 3,777,538 | 12/1973 | Weatherly et al. . |
| 3,814,102 | 6/1974 | Thal . |
| 4,043,343 | 8/1977 | Williams . |
| 4,369,788 | 1/1983 | Goald . |
| 4,440,170 | 4/1984 | Golden et al. . |
| 5,336,236 | 8/1994 | Holmes et al. .......................... 606/208 |
| 5,368,606 | 11/1994 | Marlow et al. ......................... 606/170 |
| 5,385,570 | 1/1995 | Chin et al. .............................. 606/170 |

FOREIGN PATENT DOCUMENTS 6935459 of 0000 Germany .

Primary Examiner—Michael Powell Buiz
Assistant Examiner—Kevin Truong
Attorney, Agent, or Firm—Barry R. Lipsitz

[57] ABSTRACT

In order to facilitate a simple assembling and disassembling of the individual parts of an instrument for surgical purposes with two working parts displaceable relative to one another and two gripping arms pivotal relative to one another, one of these arms being connected to the one working part and the other to the other working part such that during closing and opening, respectively, of the gripping arms the two working parts are displaced relative to one another, with one of the two gripping arms bearing a shaft for the pivotal mounting of the other gripping arm, it is suggested that the shaft have regions with different diameters and be displaceable such that either a region with a larger diameter or a region with a smaller diameter is operative in the region of the other gripping arm, that the other gripping arm have an insertion slot widening in the shape of a keyhole and having a narrower slide-in section and a widened bearing section for the shaft, the width thereof in the narrow slide-in section being between the diameters of the two regions of the shaft and in the circularly widened bearing section having a diameter corresponding to the larger diameter of the shaft, and that the gripping arm mounted on the shaft engage the one working part with an entraining element.

10 Claims, 3 Drawing Sheets

INSTRUMENT FOR SURGICAL PURPOSES

BACKGROUND OF THE INVENTION

The invention relates to an instrument for surgical purposes with two working parts displaceable relative to one another and two gripping arms pivotal relative to one another, one of these arms being connected to one working part and the other to the other working part such that during closing and opening, respectively, of the gripping arms the two working parts are displaced relative to one another, with one of the two gripping arms bearing a bearing shaft for the pivotal mounting of the other gripping arm which, for its part, engages the one working part with an entraining element.

Such instruments are used, for example, in so-called tubular shaft instruments or in surgical punches, in which two working parts which are displaceable parallel to one another are displaced via the two gripping arms. For this purpose, the gripping arms, which project essentially vertically to the longitudinal extension of the working parts, are pivotally connected to one another; they are mounted by means of a bearing shaft on one gripping arm. An articulated connection is provided, in addition, between one of the two gripping arms and one working part so that the pivotal movement of the gripping arm can be converted into a translational movement of the working part (U.S. Pat. No. 3,814,102).

The object of the invention is to design an instrument of this type such that the individual parts are easy to disassemble, for example, for the purpose of cleaning, despite this relatively complicated construction.

SUMMARY OF THE INVENTION

This object is accomplished in accordance with the invention, in an instrument of the type described at the outset, in that the shaft has regions of different diameters and is displaceable such that either a region with a larger diameter or a region with a smaller diameter is operative in the region of the other gripping arm, that the other gripping arm has an insertion slot widening in the shape of a keyhole and having a narrower slide-in section and a widened bearing section for the shaft, the width thereof in the narrower slide-in section being between the diameters of the two regions of the shaft and in the circularly widened bearing section having a diameter corresponding to the larger diameter of the shaft.

A construction of this type enables a secure mounting of the two gripping arms to be achieved in that the shaft engages in the widened bearing section of the entraining element with the region having a greater diameter. In this region, the displaceable working part is taken along by the entraining element. To detach the parts it is sufficient to move the bearing shaft such that the region with a smaller diameter is operative at the widened bearing section of the insertion slot; the gripping arm can then be guided along the shaft with the insertion slot so that the entraining element thereby leaves its operative connection with the working part. As soon as the shaft has left the insertion slot, a complete separation of the gripping arm takes place, on the one hand, from the other gripping arm and, on the other hand, from the entrained working part which can then easily be separated from the other working part by way of further displacement. In order to achieve this separation and, in the reverse case, a securing of the gripping arms on one another, it is sufficient for the shaft to be moved such that alternatively the regions with a larger or a smaller diameter become operative on the other gripping arm.

In this respect, it is advantageous for the shaft to be displaced under spring loading into a position, in which the region with a larger diameter is operative on the gripping arm mounted on the shaft. This is the normal working area, in which the gripping arms are mounted on one another so as to be pivotal. The shaft can be moved into a position, in which it is possible to separate the two gripping arms, only contrary to the action of this spring. When the shaft is released, the shaft will automatically be moved, once the two gripping arms have been fitted together, into the locking position, in which a separation is no longer possible.

The entraining element can, for example, dip into a recess in the working part; in a preferred embodiment it is, however, provided for the entraining element to be formed by the slide-in part of the insertion slot which engages around an entrainment member on the working part on opposite sides. In this respect, it is advantageous for the entrainment member to be a bolt extending parallel to the bearing shaft and having a circular cross section.

Furthermore, it has proven to be favorable in this respect for the insertion slot to be curved at its end so that one respective surface of the insertion slot which is arranged essentially vertically to the direction of displacement of the working part abuts on the entrainment member over the entire pivoting region of the gripping arms.

The bearing shaft can, for example, have regions with different diameters along its circumference and be rotatable about its longitudinal axis. For example, a cross section is conceivable which starts from a circular cross section, whereby the shaft is flattened on opposite sides. This flattening will be selected such that the shaft passes through the slide-in section of the insertion slot in the one angular position but not in the other angular position. This means that locking can be achieved simply by rotating the shaft following insertion of this gripping arm.

Another, preferred embodiment provides for the shaft to be mounted on the gripping arm for axial displacement and for the regions of different diameters to be arranged next to another in axial direction of the shaft. In this case, regions of the shaft having different diameters are moved by way of axial displacement of the shaft into the region of the insertion slot.

It is favorable for the shaft to protrude beyond the mounted gripping arm at least by the axial path of displacement of the shaft. This means that it is possible for the axial displacement to take place by pressing on the protruding part, namely to such an extent until the shaft is displaced into the release position.

In this respect, it can also be provided for the shaft to have, in the region protruding beyond the mounted gripping arm, a diameter which is larger than the diameter of the widened bearing section of the insertion slot. On the one hand, this facilitates handling since the operator has a pressure surface available which can be adequately large, even when the shaft has a very small diameter; on the other hand, this region with a larger diameter can be used as a stop which limits the depth of insertion of the shaft.

BRIEF DESCRIPTION OF THE DRAWINGS

The following description of preferred embodiments of the invention serves to explain the invention in greater detail in conjunction with the drawings. In the drawings.

DETAILED DESCRIPTION OF THE INVENTION

Figure 1:
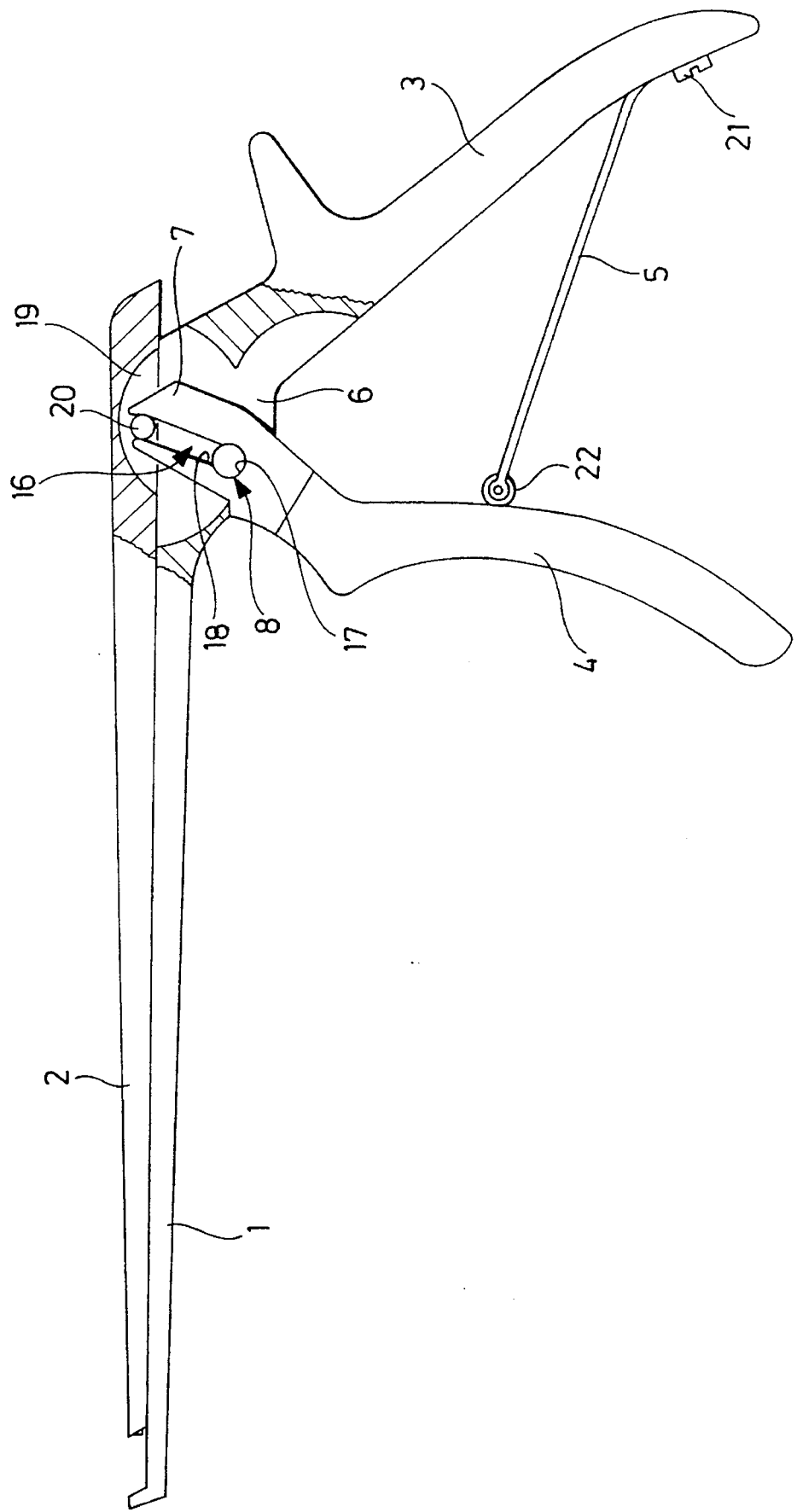
FIG. 1 is a schematic side view of a surgical instrument.

The instrument illustrated in the drawings has two elongated working parts 1 and 2 which are displaceable parallel to one another due to a longitudinal guide means not illustrated in the drawings. This can, for example, be a tissue punch, with punch-like tools arranged at the free ends of both the working parts 1 and 2, these tools gripping tissue lying between the two working parts 1 and 2 when these are moved relative to one another and punching a piece out of this tissue.

The lower working part 1 is integrally connected to a gripping arm 3, on which a second gripping arm 4 is pivotally mounted about a pivot axis extending transversely to the longitudinal direction of the working parts 1 and 2. A cantilever spring 5 is arranged between the two gripping arms and this spring separates the two gripping arms from one another so that the two gripping arms 3 and 4 can be pivoted towards one another contrary to a spring force.

For the purpose of mounting the gripping arm 4 on the gripping arm 3, the gripping arm 3 has a slot 6 which extends parallel to the longitudinal direction of the working parts 1 and 2 and is continuous from top to bottom. A tongue 7 integrally formed on the other gripping arm 4 dips into this slot and the width of this tongue corresponds essentially to the width of the slot 6 so that the gripping arm 4 is laterally secured in this slot In the region of mounting, the gripping arm 3 bears a shaft 8 which is longer than the width of the gripping arm 3 and therefore protrudes on both sides beyond the gripping arm 3. On the one side, the shaft 8 engages with a cup-shaped end 9 in a bowl 10 which is pressed into a stepped bore 11 in the gripping arm 3. This stepped bore 11 passes through the entire gripping arm 3; it has a widened region on one side where the bowl 10 is fitted into the bore. The remaining area of the stepped bore 11 having a smaller diameter corresponds in its interior diameter to the interior diameter of the bowl 10 which also corresponds to the external diameter of the cup-shaped end 9 and the oppositely located end 12 of the shaft 8. This means that the shaft 8 is freely displaceable in axial direction in the bowl 10 and in the stepped bore 11 but is secured in radial direction.

A helical spring 13 partially enclosed by the cup-shaped end 9 of the shaft 8 is arranged in the bowl 10; this spring is supported on the base of the bowl 10 and on the end face of the shaft 8 and thus acts on the shaft 8 with a force issuing from the bowl 10.

In the region between the cup-shaped end 9 and the end 12 of the shaft, this has two adjacently located regions with a smaller diameter, namely one region 14 adjoining the end 9 and one region 15 adjoining the end 12, the diameter of which is even smaller than that of the region 14. The regions 14 and 15 each extend in axial direction over a distance which is greater than the width of the slot 6.

An insertion slot 16 widening in the shape of a keyhole is arranged in the tongue 7 of the gripping arm 4 and this slot has a bearing section 17 circular in cross section and a slide-in section 18 exiting radially therefrom. This section is designed essentially in a straight line; only at the upper end of the tongue does the slide-in section 18 have a slight curvature. The diameter of the bearing section 17 corresponds to the diameter of the region 14 on the shaft 8, the width of the slide-in section 18 corresponds to the diameter of the region 15 of the shaft 8.

A slot 19 is likewise worked into the upper working part 2, aligned with the slot 6 in the gripping arm 3, and a bolt 20 which is circular in cross section and extends parallel to the shaft 8 passes through this slot.

Assembly of the parts of the instrument described commences with the two working parts 1 and 2 being displaced parallel to one another along their relative guide means such that the bolt 20 is located approximately above the stepped bore 11. Subsequently, the front gripping arm 4 is inserted into the slot 6 from below with its tongue 7 until the end of the slide-in section 18 strikes against the shaft 8. Due to the action of the helical spring 13, the region 14 with the larger diameter is located at the end of the slide-in section 18 and so no further displacement of the tongue 7 is possible. To enable the tongue 7 to be pushed in further, the shaft 8 is moved into the bowl 10 contrary to the action of the helical spring 13 by pressing on its end 12 until the region 15 with the smaller diameter bridges the slot 6. Since the diameter of the region 15 is equal to or slightly smaller than the width of the slide-in section 18, the tongue 7 can now be pushed into the slot 6 to such an extent until the end of the slide-in section 18 engages around the bolt 20 on both sides and until the shaft 8 reaches the bearing section 17 of the insertion slot 16. If the shaft 8 is released in this position, it will be displaced axially due to the action of the helical spring 13, and the region 14 with the larger diameter enters the bearing section 17, the diameter of which corresponds essentially to that of the region 14. This results in a perfect mounting of the gripping arm 4 on the gripping arm 3. The cantilever spring 5 which is, for example, secured on the gripping arm 3 with a screw 21 can be suspended in a releasable holder 22 on the gripping arm 4 or it abuts on the gripping arm 4 via a roller; with that the instrument is ready for use. When the gripping arm 4 is pivoted relative to the gripping arm 3, the bolt 20 is taken along the path of displacement of the working part 2 and can thereby be moved in longitudinal direction in the slide-in section 18 of the insertion slot 16; this bolt 20 therefore forms an entrainment member which cooperates with the insertion slot 16 forming an entraining element. In this respect, it is essential that the translational movement of the working part 1 can take place unhindered, i.e. the bolt 20 can move along a straight line while the insertion slot 16 is pivoted about the pivot axis determined by the shaft 8.

Detachment can take place in the reverse direction in that the shaft 8 is axially displaced contrary to the helical spring 13 to such an extent until the region 15 with a smaller external diameter bridges the slot 6. It is then possible without difficulty, where necessary after releasing the holder 22, to withdraw the gripping arm 4 out of the slot 6 along the insertion slot 16. Once the gripping arm 4 has been removed, the upper working part 2 can also be pushed out completely towards the rear relative to the lower working part 1.

Figure 2:
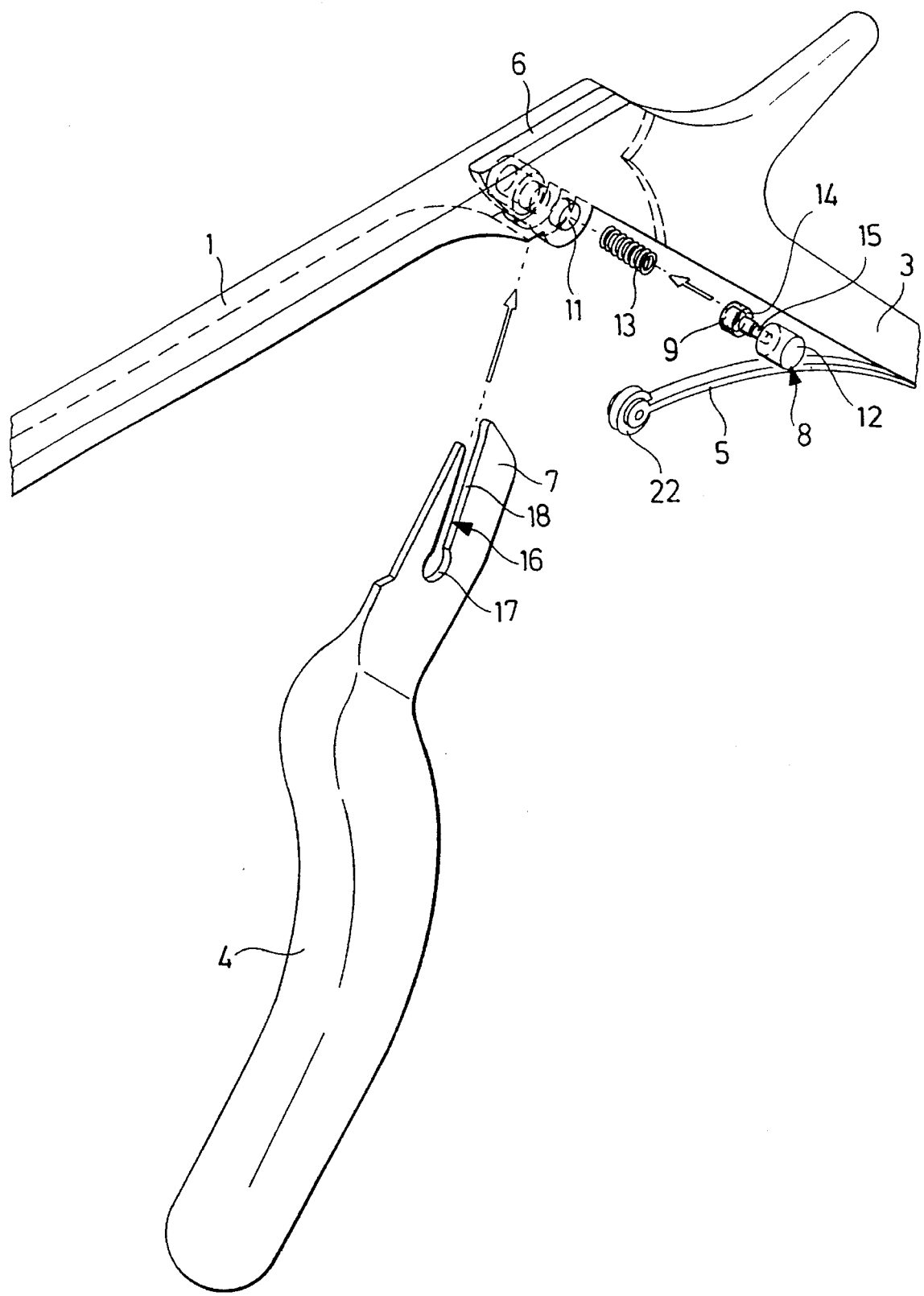
FIG. 2 is a view of the instrument from FIG. 1 in the end region in the disassembled state.
Figure 3:
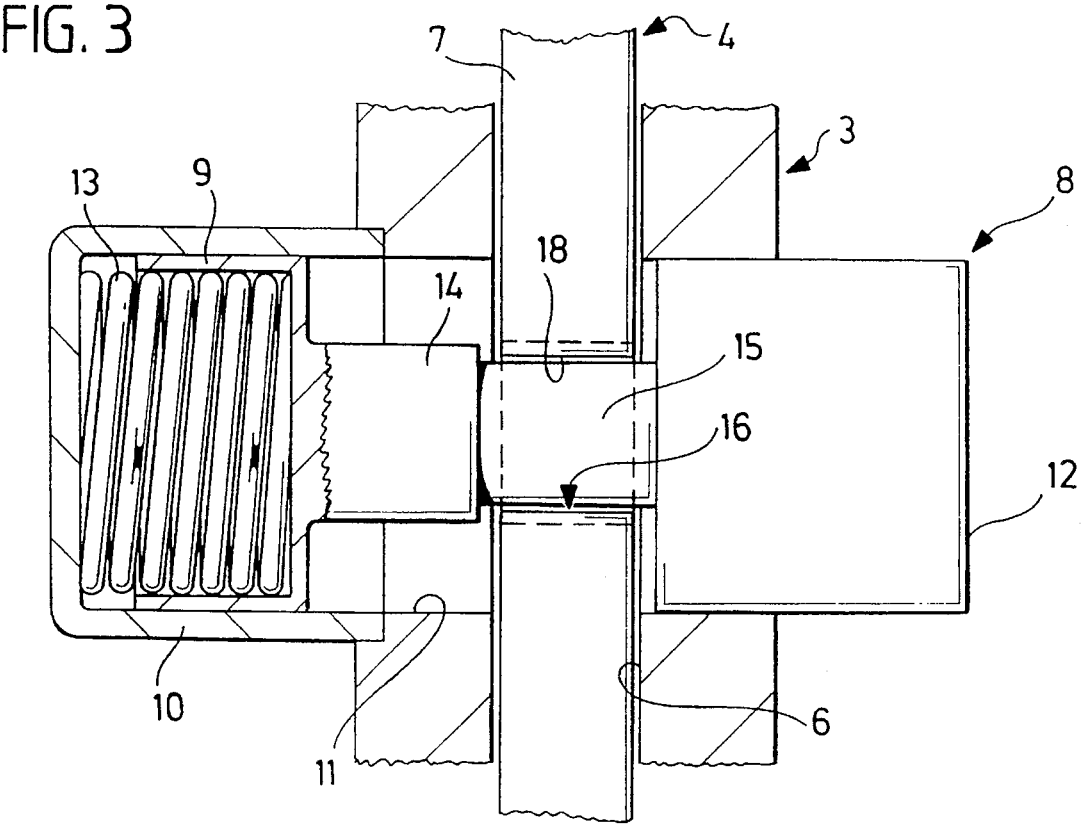
FIG. 3 is a longitudinal, sectional view of the instrument from FIG. 1 in the mounting region of the two gripping arms with the shaft in the unlocked state
Figure 4:
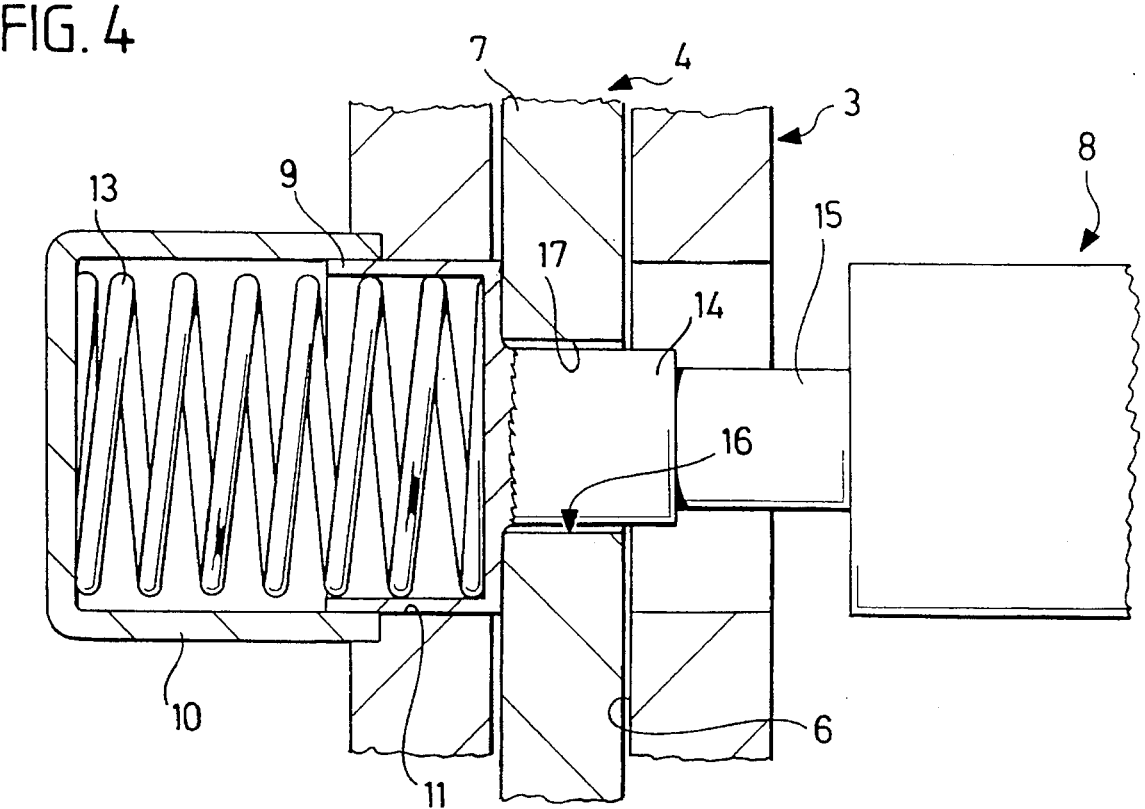
FIG. 4 is a view similar to FIG. 3 with the bearing shaft in the locked state.

As shown by the illustration in FIG. 2, it is fundamentally also possible to remove the shaft 8 for cleaning purposes; this can be done following the withdrawal of the front gripping arm 4 simply by pulling the shaft 8 out through the stepped bore 11; the helical spring 13 can also be withdrawn out of the bowl 10 in the same manner once the shaft 8 has been removed.

In this way, a particularly simple mounting is obtained which can quickly be released and provided and with which all the individual parts can be assembled and disassembled for cleaning purposes in the simplest manner.

I claim:

1. An instrument for surgical purposes with two working parts displaceable relative to one another and two gripping arms pivotal relative to one another, one of said arms being connected to one of said working parts and the other of said arms being connected to the other working part such that during closing and opening, respectively, of the gripping arms the two working parts are displaced relative to one another, wherein one of the two gripping arms bears a shaft for the pivotal mounting of the other gripping arm, said other gripping arm engaging the working part connected thereto via an entraining element, wherein the shaft has regions with different diameters and is displaceable such that either a region with a larger diameter or a region with a smaller diameter is operative in a region of the other gripping arm, that the other gripping arm has an insertion slot widening in the shape of a keyhole and having a narrower slide-in section and a circularly widened bearing section for the shaft, the width thereof in the narrower slide-in section being between the diameters of the two regions of the shaft and in the circularly widened bearing section having a diameter corresponding to the larger diameter region of the shaft.

2. An instrument as defined in claim 1, wherein the shaft is displaced under spring loading into a position wherein the region with a larger diameter is operative on the gripping arm mounted on the shaft.

3. An instrument as defined in claim 2 wherein the entraining element is formed by opposite sides of the slide-in section of the insertion slot engaging around an entrainment member of the working part connected to said other gripping arm.

4. An instrument as defined in claim 3, wherein the entrainment member is a bolt extending parallel to the shaft and having a circular cross section.

5. An instrument as defined in claim 1 wherein the entraining element is formed by opposite sides of the slide-in section of the insertion slot engaging around an entrainment member of the working part connected to said other gripping arm.

6. An instrument as defined in claim 5, wherein the entrainment member is a bolt extending parallel to the shaft and having a circular cross section.

7. An instrument as defined in claim 1, wherein the insertion slot has a curved end.

8. An instrument as defined in claim 1, wherein:

the shaft is mounted on its associated gripping arm for axial displacement; and the regions having different diameters are arranged next to one another in the axial direction of the shaft.

9. An instrument as defined in claim 8, wherein the shaft protrudes beyond the gripping arm mounted thereon at least by the maximum axial path of displacement of the shaft.

10. An instrument as defined in claim 9, wherein in the region protruding beyond the gripping arm mounted thereon, the shaft has a diameter larger than the diameter of the widened bearing section of the insertion slot.

* * * * *